United States Patent [19]

Du Vall et al.

[11] 3,933,147

[45] Jan. 20, 1976

[54] APPARATUS AND METHOD FOR TREATING DISORDERS IN THE REGION OF THE PUBOCOCCYGEOUS MUSCLE

[76] Inventors: Wilbur E. Du Vall, 22710 Pennsylvania Ave., Torrance, Calif. 90501; Roger J. Foster, 26614 Menominee Place, Palos Verdes, Calif. 90274

[22] Filed: Apr. 2, 1970

[21] Appl. No.: 25,022

[52] U.S. Cl.................. 128/2 S; 128/2 N; 128/408; 128/421
[51] Int. Cl.²........................ A61B 5/10; A61N 1/32
[58] Field of Search.......................... 128/407–409, 128/421–422, 303.13, 2 R, 2 S, 2 N

[56] References Cited
UNITED STATES PATENTS

| | | | |
|---|---|---|---|
| 7,668 | 7/1833 | Harrington.......................... | 128/404 |
| 539,501 | 5/1895 | Boyd........................... | 128/303.13 X |
| 870,927 | 11/1907 | Boyd................................ | 128/407 |
| 1,042,624 | 10/1912 | Wagoner............................. | 128/407 |
| 2,532,788 | 12/1950 | Sarnoff.............................. | 128/421 |
| 3,185,939 | 5/1965 | Moss et al.......................... | 128/422 |
| 3,295,515 | 1/1967 | Kahn............................... | 128/2.06 E |
| 3,403,684 | 10/1968 | Stiebel et al....................... | 128/407 |
| 3,474,775 | 10/1969 | Johnson............................ | 128/2.1 |
| 3,474,776 | 10/1969 | O'Brien............................. | 128/2 R |
| 3,480,003 | 11/1969 | Crites............................... | 128/2 R |
| 3,516,413 | 6/1970 | McDonald et al.................. | 128/422 |
| 3,640,284 | 2/1972 | DeLangis............................ | 128/422 |

FOREIGN PATENTS OR APPLICATIONS

| | | | |
|---|---|---|---|
| 361,806 | 10/1906 | France.............................. | 128/421 |
| 1,947,412 | 6/1970 | Germany........................... | 128/408 |
| 1,145,749 | 3/1969 | United Kingdom................. | 128/407 |
| 206,002 | 4/1968 | U.S.S.R............................. | 128/408 |

*Primary Examiner*—Kyle L. Howell
*Attorney, Agent, or Firm*—Lindenberg, Freilich, Wasserman, Rosen & Fernandez

[57] ABSTRACT

An electrical applicator for applying currents that cause repeated involuntary contractions of the pubococcygeous muscle. The repeated current applications are used to treat muscle structures that have been damaged during childbirth and/or weakened from disuse, and which have contributed to the pathological formation of cyctocoel, rectocoel, uterine prolapse, and bladder malfunctions. A probe is provided which is connected to a pulse generator that applies trains of pulses at intervals such as every two seconds, every train lasting for about one second and containing pulses of a repetition rate such as 200 pulses per second. The apparatus further includes means for sensing the intensity of muscle contractions.

1 Claim, 7 Drawing Figures

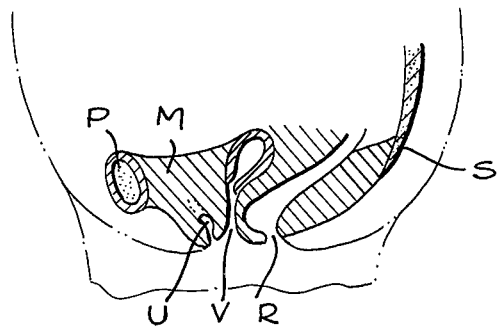
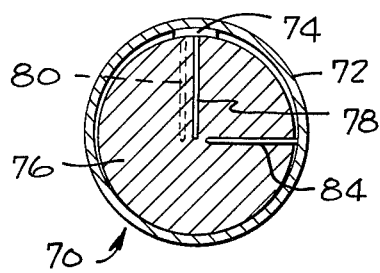
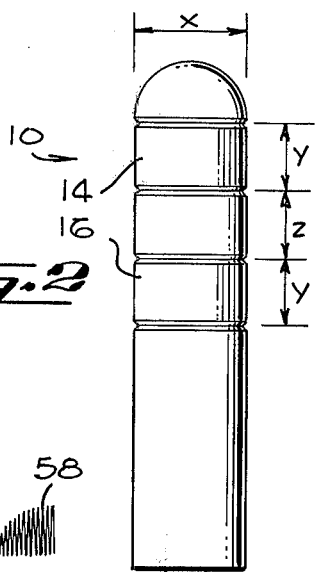
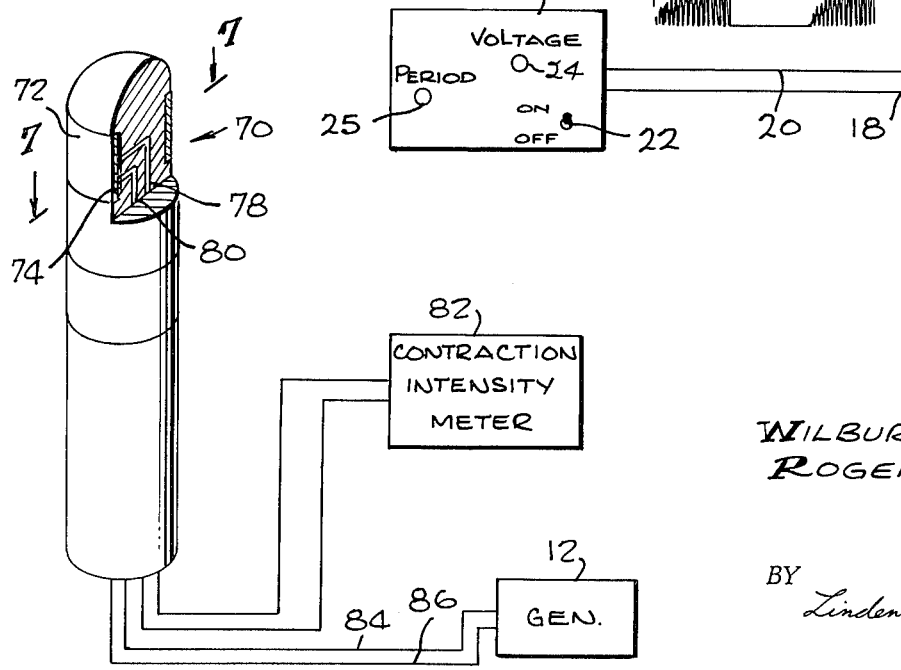

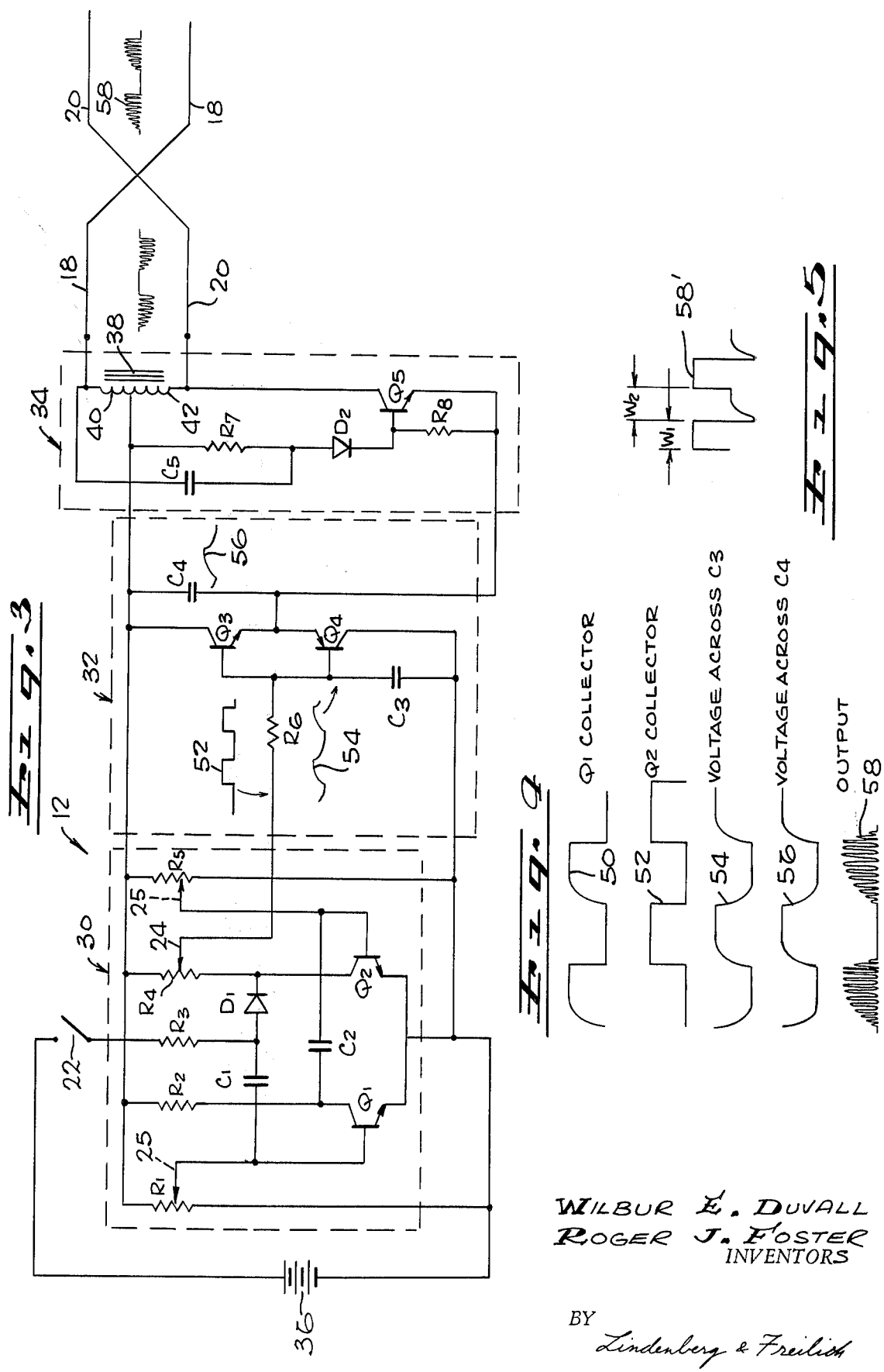

APPARATUS AND METHOD FOR TREATING DISORDERS IN THE REGION OF THE PUBOCOCCYGEOUS MUSCLE

BACKGROUND OF THE INVENTION

1. Field of the Invention:

This invention relates to electrical applicators and to apparatus and methods for treating disorders in the pelvic muscle supporting structures of the female body.

2. Description of the Prior Art:

The urethra, vagina, and rectum are largely supported by the pubococcygeous muscle. This muscle originates from the symphsis pubis, a bone structure at the front of the abdomen, extends posteriorly, encompassing the urethra, the vagina, and the rectum, and inserts in the coccyx and inferior portion of the sacrum. The pubococcygeous muscle is sometimes damaged during childbirth or becomes weakened from disuse. This contributes to the pathological formation of cyctocoel (hernial protrusion of the urinary bladder through the vaginal wall), rectocoel (hernial protrusion of part of the rectum into the vagina), uterine prolapse (protrusion of the uterus through the vaginal orifice), and bladder malfunctions. It has been found that these pathological conditions can be helped when normal muscle tone is established in the pubococcygeous muscle.

One procedure for improving the tone of the pubococcygeous muscle is for the patient to repeatedly voluntarily contract the muscle. However, while the pubococcygeous muscle can be voluntarily contracted, patients sometimes find it difficult to perform such contractions or to perform them with substantial intensity. This may be due to the weakened state of the muscle and to long periods of disuse that lead to unfamiliarity in control of the muscle. Some types of voluntary exercises have been prescribed, such as the exercises developed by Dr. Arnold Kegel of the University of California, where the patient tries to repeatedly cease the outflow of urine. However, the voluntary exercises alone may not improve muscle tone sufficiently, particularly where the patient does not comprehend the intensity of contractions required.

OBJECTS AND SUMMARY OF THE INVENTION

One object of the present invention is to provide apparatus for improving the condition of the pubococcygeous muscle.

In accordance with one embodiment of the present invention, apparatus is provided for treating disorders arising from a condition of a weakened pubococcygeous muscle. The apparatus includes a probe for insertion in the vagina, and an electronic generator connected to electrodes on the probe for carrying currents to it that are applied to the pubococcygeous muscle to contract it. The currents comprise trains of pulses at a frequency such as 200 pulses per second, the envelope of each pulse train rising gradually from zero volts to about 10 volts in about one quarter second and continuing at this level for about three-quarters of a second. Thus, each train of pulses lasts for a period such as 1 second, which is sufficient for the pubococcygeous muscle to substantially fully contract. The current is then stopped for a period such as 1 second, for the muscle to substantially fully relax. Another train of pulses is then delivered to the probe to repeat the cycle.

One method for treating pathological conditions of the pelvic supporting muscle structures, and particularly a weakened condition of the pubococcygeous muscle, involves coating the prove with an electrically conductive lubricant, inserting the probe into the vagina, and retaining the probe therein for a period such as 20 minutes while the apparatus is repeatedly cycled, to provide many involuntary contractions. Such treatment is repeated at intervals such as every several days. In addition, exercises are prescribed involving voluntary contractions of the pubococcygeous muscle, to be performed between visits to the physician where the probe treatment is given. The involuntary contractions during probe treatment not only tone the pubococcygeous muscle, but make the patient aware of the type of contraction and intensity which may be employed during voluntary exercise, or during use of the muscle in normal bodily functions including urination, defecation and intercourse.

The novel features of the invention are set forth with particularity in the appended claims. The invention will be best understood from the following description when read in conjunction with the accompanying drawings.

BRIEF DESCRIPTION OF THE DRAWINGS

FIG. 1 is a sectional side view of a portion of the female human body, showing the location of the pubococcygeous muscle relative to the urethra, vagina, and rectum;

FIG. 2 is a view of a probe and generator constructed in accordance with the invention;

FIG. 3 is a circuit diagram of the generator of FIG. 2;

FIG. 4 is a representation of waveforms in the generator of FIG. 3;

FIG. 5 is a detailed view of a portion of the output waveform shown at 58 in FIG. 4;

FIG. 6 is a sectional perspective view of a probe and sensor for measuring the strength of muscle contractions, constructed in accordance with another embodiment of the invention; and FIG. 7 is a view taken on the line 7—7 of FIG. 6.

DESCRIPTION OF THE PREFERRED EMBODIMENTS

As shown in FIG. 1, the pubococcygeous muscle M originates from the symphsis pubis P, extends posteriorly encompassing the urethra U, the vagina V, and the rectum R, and inserts in the coccyx and inferior portion of the sacrum S. While other muscles are employed in the support and functioning of the urethra, vagina and rectum, the pubococcygeous muscle is the main or most powerful muscle in this region of the female body. The pubococcygeous muscle often works in conjunction with other muscles, for example, the sphincter urethrae can work in conjunction with the pubococcygeous muscle to control urination. Many pathological conditions such as cystocoel, rectocoel, uterine prolapse, and bladder malfunctions may be caused by a weakened condition of the pubococcygeous muscle. While exercises involving voluntary constrictions of this muscle can help improve its condition, such exercises may be difficult to perform by a patient whose muscle is in a very weakened condition and/or who does not know how to correctly contract it. In addition, patients generally will not exercise for long, regular periods at substantial intensity, which is required to significantly improve the tone of the muscle.

As illustrated in FIG. 2, a probe 10 is provided to apply electrical currents from a generator 12 to the pubococcygeous muscle. The probe 10 is constructed of an electrically insulative material such as an ordinary plastic, but has a pair of ring-shaped electrodes 14, 16 thereon which are substantially flush with regions of the probe in front and behind them along the length of the probe. A pair of electrical conductors 18, 20 lead from the generator 12 and into the probe, where they are connected to the electrodes thereof. When the probe is inserted into the vagina V, the electrodes 14, 16 make electrical contact with spaced portions of the pubococcygeous muscle M. Currents supplied to the muscle M cause it to contract involuntarily, but in a manner similar to the manner in which it may be voluntarily contracted.

The generator 12 is constructed to provide currents in repetitious cycles, each cycle having a duration T such as two seconds. During a first portion of each cycle, which may last for a period $D_1$ such as one second, the generator delivers a train of pulses at a rate such as 200 pulses per second. During the last portion $D_2$ of each cycle, the generator does not deliver a current. These cycles may be repeated for many minutes, until the treatment is terminated.

A physician may administer a treatment by first coating the probe 10 with a lubricant which is of moderate electrical conductivity, such as a mixture of an ordinary medical lubricating jelly and a saline solution. He then turns on the generator 12, and adjusts a voltage control 24 to zero volts and a period control 25 to the longest period. The physician inserts the probe into the vagina and has the patient thereafter hold the probe in place with her hands. The physician then adjusts the voltage control 24 to a level which produces strong contractions without pain, such as 10 volts, and adjusts the period T of each cycle to about the shortest period that is still comfortable to the patient. Generally, the rest period $D_2$ of each cycle must be sufficient to enable substantially complete muscle relaxation, in order for the treatment to be as comfortable as possible. After a period of at least several minutes, such as twenty minutes, the treatment is stopped.

Such treatments may be repeated at intervals such as every two or three days. The physician generally prescribes voluntary exercises to be performed between probe treatments. For example, the patient may be directed to contract the pelvic area muscle structure ten times in succession each morning before getting out of bed. The physician may advise that the muscle structure should be contracted to approximately the same tightness, or intensity, and in the same region of the body, as is achieved during probe treatment. The patient learns what effect should be sensed when the pubococcygeous muscle is contracted substantially, by her experience with the probe treatment. In addition, the probe treatment itself will have exercised the muscle structure.

The current pulses delivered through the probe are at a repetition rate such as 200 pulses per second. It has been found that with a pulse rate less than about 100 pulses per second, the effect on some patients is to induce a feeling that they must urinate. This feeling can become stronger as the pulse period decreases towards an unmodulated or constant level pulse. It also has been found that with a pulse rate greater than about 400 pulses per second, many patients experience a burning sensation. Thus, it is preferable to utilize a rate within the range of about 100 to 400 pulses per second. A rate of about 200 pulses per second or 200 Hz. is generally preferred. The maximum voltage of each pulse train should be high enough to induce moderately strong contractions. In many cases, after insertion of the probe, the physician immediately increases the voltage to about 8 or 9 volts (for a probe with electrodes 14, 16 separated by about ¾ inch). After about 15 minutes at this level, the voltage may have to be increased to 10¼ or 11 volts in order to maintain strong contractions. If the pubococcygeous muscle is initially very weak, the physician may have to begin (after insertion in the vagina) with about a 12 volt level. In any case, the voltage should not be so high as to produce violent contractions. The envelope of each pulse train preferably rises smoothly from zero to maximum voltage, in an appreciable period, such as one-quarter second, and preferably during at least one-tenth of each pulse train (i.e., during at least five pulses in a 200 Hz pulse train that lasts for only one-quarter second). This is to induce smooth muscle contractions and avoid sudden jolts of muscle contraction.

The duration of each current pulse train should be long enough to substantially completely contract the muscle structure. A train of at least about one-quarter second duration is generally desirable to substantially completely contract the pubococcygeous muscle, although a longer duration such as up to about 1½ seconds may be desirable in some individuals. In a similar manner, the rest time in each cycle, when no pulses are delivered through the probe, should be long enough to allow the muscle to substantially completely relax. A rest period of at least about one-quarter second is generally preferred to permit such relaxation, although a longer time up to about 1½ second may be necessary in some individuals. Thus, each complete cycle will generally range from about ½ to 3 seconds. A longer cycle period than three seconds will generally still be comfortable, but it wastes time. The cycle period may be adjusted to the shortest period which is comfortable to the patient, to best utilize the time. It may be noted that even for a 3 second cycle, there will be approximately 400 muscle contractions in a 20 minute treatment.

FIG. 3 illustrates the circuit of the pulse generator 12 which generates the pulses delivered to the probe. The circuit may be considered as having three major portions, these being a low frequency square wave generator 30 operating at a rate of approximately 1 Hz (1 pulse per second), an emitter follower 32 which shapes the square wave, and a higher frequency oscillator 34 which modulates the shaped square wave by a higher frequency signal of approximately 200 Hz (200 pulses per second). The cycle rate, which is determined by the low frequency generator 30 can be varied within a predetermined range, such as between about 2 Hz and about 0.3 Hz (½ second per cycle to 3 seconds per cycle) by adjusting the control 25 that moves the wipers of potentiometers $R_1$ and $R_5$. The maximum voltage of each pulse train can be varied by adjusting the wiper 24 of a potentiometer $R_4$. The generator can be turned on and off by the switch 22. The circuit may be operated by a low voltage battery 36 such as one of 12 volts. The use of a low voltage battery instead of the common 110 volt household supply, not only reduces the possibility of harmful shock in case of a short circuit, but can ease any worry of the patient about the possibility of a large shock.

Considering the circuit in detail and beginning with the square wave generator 30, potentiometer, or variable resistor $R_1$ supplies bias current to transistor $Q_1$ while resistor $R_2$ serves as the collector load of $Q_1$. Similarly, potentiometer, or variable resistor $R_5$ supplies bias current to the base of transistor $Q_2$, while resistor $R_4$ serves as the collector load of $Q_2$. Resistor $R_3$ and diode $D_1$ form an isolation circuit to isolate the charging path of a capacitor $C_1$ from the output of $Q_2$. Capacitors $C_1$ and $C_2$ are connected to provide positive (regenerative) feedback to cause oscillations.

When switch 22 is closed, transistors $Q_1$ and $Q_2$ will both start to conduct, since their base resistors $R_1$ and $R_5$ supply bias current. One of the transistors $Q_1$ or $Q_2$ will start to draw slightly more collector current than the other, and that transistor will provide a signal tending to turn off the other transistor and tending to turn itself further on. This rapid regeneration action results in one transistor turning completely on (to saturation) and the other turning completely off. During the time one transistor such as $Q_1$ is completely on, the capacitor $C_2$ coupling its collector to the base of the fully off transistor discharges through the base resistor $R_5$ of the fully off transistor. When that capacitor $C_2$ is fully discharged, the off transistor $Q_2$ will start to conduct and supply a signal through capacitor $C_1$ tending to turn off the transistor $Q_1$, and turn itself fully on. The alternate conduction and cutoff of the transistors is at frequencies determined by the capacitors, the time of a first half of a cycle being determined by the discharging time through $C_1$ and $R_1$, and the time of the second half of a cycle being determined by the discharging time through $C_2$ and $R_5$.

The voltage waveform on the collector of $Q_1$ (see waveform 50 in FIG. 4) is a square wave with an exponential rise on the positive-going edge due to the charging of capacitor $C_2$ through $R_2$. However, the voltage waveform on the collector of $Q_2$ (shown at 52 in FIG. 4) is a square wave with very fast rise and fall times. The positive-going edge of the signal at the collector of $Q_2$ will not be exponential because the charge current for $C_1$ is supplied by $R_3$ and not by $R_4$. During the charging of capacitor $C_1$, diode $D_1$ is back-biased (nonconducting), since this diode conducts only when $Q_2$ is conducting. The square wave generated by the circuit portion containing $Q_1$ and $Q_2$ is taken from the wiper of the potentiometer $R_4$, and it passes to the emitter follower portion 32 of the generator where it is shaped.

The square wave taken from the wiper of potentiometer $R_4$ is carried through resistor $R_6$ to the base of NPN transistor $Q_3$ and PNP transistor $Q_4$. The resistor $R_6$ also couples the square wave to an integrating capacitor $C_3$. It should be noted that the $C_3$, $R_6$ combination determines the rise and fall times of the square wave voltages at the bases of $Q_3$ and $Q_4$. The waveform across capacitor $C_3$ is duplicated across capacitor $C_4$ by reason of emitter follower operation of transistors $Q_3$ and $Q_4$. $C_4$ serves as a storage capacitor for supplying the output transistor $Q_5$ and associated components of the following higher frequency oscillator portion 34.

The oscillator portion 34 provides a higher frequency (e.g. 200 Hz) signal that modulates the signal across capacitor $C_4$. During the last half of a cycle period, when the voltage across $C_4$ is zero, there is no power to transistor $Q_5$ and it does not deliver pulses. However, at the beginning of the next cycle, when a voltage begins to appear across $C_4$, transistor $Q_5$ starts to conduct. Base current to $Q_5$ to supplied through $R_7$ and diode $D_2$.

When $Q_5$ starts to conduct, its collector voltage starts to drop. The transformer 38 is wound so that when the end 42 drops in voltage, the opposite end 40 goes positive, thus increasing the current through $Q_5$. This regenerative action continues until $Q_5$ is fully saturated. $Q_5$ remains saturated only so long as its collector current can increase. However, when the collector current of $Q_5$ reaches a maximum the voltage at 40 begins to fall, this drop being coupled through $C_5$ and $R_7$. Diode $D_2$ then becomes non-conducting (back-biased) and $Q_5$ is turned off. $Q_5$ remains off until $C_5$ discharges through $R_7$. As soon as $C_5$ is fully discharged, $Q_5$ starts to conduct again, and the cycle is repeated. These cycles continue as long as there is a voltage across $C_4$.

In the output of oscillator 34, whose waveform is shown at 58 with one pulse of a pulse train shown in FIG. 5, the width $W_1$ of the modulating pulses is determined by the inductance of the transformer winding between end 42 and the point connected to $C_4$. The spacing $W_2$ between pulses is determined by the discharge time of $C_5$ through $R_7$. The final output delivered to the probe is taken across the ends of transformer 38, by conductors 18 and 20 that connect to the probe.

A variety of circuits can be employed to generate pulse trains for application through the probe to the body. For example, a sinusoidal oscillator can be used to modulate the output of a low frequency generator, to provide trains of sinusoidal pulses. However, a square wave type of oscillator or pulse generator of the type shown in FIG. 3 at 32, generally can be produced at lower cost.

The generator 12 therefore provides trains of current pulses of a repetition rate on the order of 200 Hz, each train lasting for a period such as one second and being followed by a rest period such as one second when no appreciable pulses are delivered. The envelope of each train of pulses rises gradually so that there are at least about five pulses of a voltage less than 90% of the maximum envelope voltage in each train. The maximum voltage of the pulse trains is adjustable from zero to about 12 volts, the pulse level used during treatment generally ranging between about 8 volts for patients with a moderately well toned muscle structure (for a probe with electrodes spaced about ¾ inch) to about 12 volts for patients with a very poorly conditioned muscle structure or for use near the end of a treatment cycle. The time of each cycle, which includes a pulse train and a rest period, can be readily altered by the physician to what is comfortable to the patient, and typically ranges from about ½ second to about 3 seconds.

A diameter X for the probe of about 1 inch generally readily enables insertion into the vagina while allowing for good electrical contact of the electrodes 14, 16 with the vagina walls. A length Y of about three-quarter inch for each electrode, and a spacing Z of about three-quarter inch between them has been found to provide good current applications.

FIGS. 6 and 7 illustrate a probe 70 constructed in accordance with another embodiment of the invention, which not only allows the application of contraction-inducing currents, but enables measurements to be made of the strength of the muscle contractions. The probe 70 includes one electrode 72 constructed of a thin band of resilient material such as 0.002 inch thick stainless steel. A strain gauge 74 disposed between the core 76 of the probe and one side of the band 72, enables measurements to be made of contracting forces applied to that portion of the band. Strain gauge leads 78, 80 extend through the probe to a contraction intensity meter 82. This meter 82 can be a bridge which employs the strain gauge as one bridge arm, or even a battery and voltmeter combination. The probe assembly also includes conductors 84, 86 that lead from the generator 12 to the electrodes to apply currents to them, as described above.

The prove 70 should be inserted so that the strain gauge 74 is oriented in the direction in which the walls of the vagina contract to the greatest extent. This probe can be used to measure voluntary contractions as well as involuntary contractions, and can be employed to measure the muscle tone before and in the course of a series of treatments.

While the probes are generally inserted in the vagina, they could be inserted in the rectum, since the pubococcygeous muscle also extends around the rectum. However, application to the vagina is generally more comfortable.

Although particular embodiments of the invention have been described and illustrated herein, it is recognized that modifications and variations may readily occur to those skilled in the art and, consequently, it is intended that the claims be interpreted to cover such modifications and equivalents.

What is claimed is:

1. Apparatus for treating a muscle in the pelvic region comprising:
    a probe of a width on the order of an inch to permit insertion into the adult human vagina, said probe having spaced electrode means thereon for applying currents to the body and strain gauge means for sensing the intensity of muscle contractions that tend to compress the electrodes;
    a generator coupled to said electrode means, said generator constructed to generate trains of pulses at a repetition rate within the range of 100 per second to 400 per second; and
    meter means coupled to said strain gauge means for providing an indication of the level of intensity of muscle contractions.

* * * * *